United States Patent [19]

Gordon et al.

[11] 4,415,288

[45] Nov. 15, 1983

[54] LIQUID DISPENSING DEVICE WITH CARTRIDGE-RUPTURING MEMBER

[75] Inventors: Marvin Gordon, East Windsor; Joseph Lichtenstein, Colonia, both of N.J.

[73] Assignee: Whitman Medical Corporation, Clark, N.J.

[21] Appl. No.: 298,246

[22] Filed: Aug. 31, 1981

Related U.S. Application Data

[63] Continuation-in-part of Ser. No. 241,486, Mar. 9, 1981, abandoned.

[51] Int. Cl.³ .................... A47L 13/17; A61M 35/00
[52] U.S. Cl. ................................... 401/132; 401/133; 401/134; 401/156; 401/196; 604/3
[58] Field of Search .................. 401/132–135, 401/156, 196; 128/267, 269; 604/3

[56] References Cited

U.S. PATENT DOCUMENTS

| | | | |
|---|---|---|---|
| 195,719 | 10/1877 | Might et al. | 401/156 |
| 849,110 | 4/1907 | Erickson | 401/134 |
| 2,987,743 | 6/1961 | Capps | 401/135 |
| 3,061,868 | 11/1962 | Miller | 401/135 |
| 3,399,019 | 8/1968 | Koelichen | 401/134 |
| 3,481,676 | 12/1969 | Schwartzman | 401/134 |
| 3,847,151 | 11/1974 | D'Alessandro | 128/269 |
| 3,876,314 | 4/1975 | Nehring | 401/133 |
| 3,981,304 | 9/1976 | Szpur | 401/133 X |
| 4,155,663 | 5/1979 | Cerquozzi | 401/135 |

FOREIGN PATENT DOCUMENTS

| | | | |
|---|---|---|---|
| 1187954 | 2/1965 | Fed. Rep. of Germany | 401/133 |
| 1757467 | 5/1973 | Fed. Rep. of Germany | 401/134 |

Primary Examiner—Steven A. Bratlie
Attorney, Agent, or Firm—Holman & Stern

[57] ABSTRACT

An improved liquid dispensing device having particular utility as a surgical scrub and/or swab unit is characterized by a cartridge which is slidable in a rigid handle and rupturably by a spike when slid within the handle to a predetermined degree. Fluid from the ruptured cartridge flows from within the handle to within a sponge through apertures which permit free flow of the dispensed fluid. The handle may be provided with longitudinally-extending slots to facilitate compression of the handle and the cartridge disposed therein. A check valve may be included in the hollow spike passage to prevent back flow of liquid from the sponge and dispensing chamber into the cartridge.

3 Claims, 8 Drawing Figures

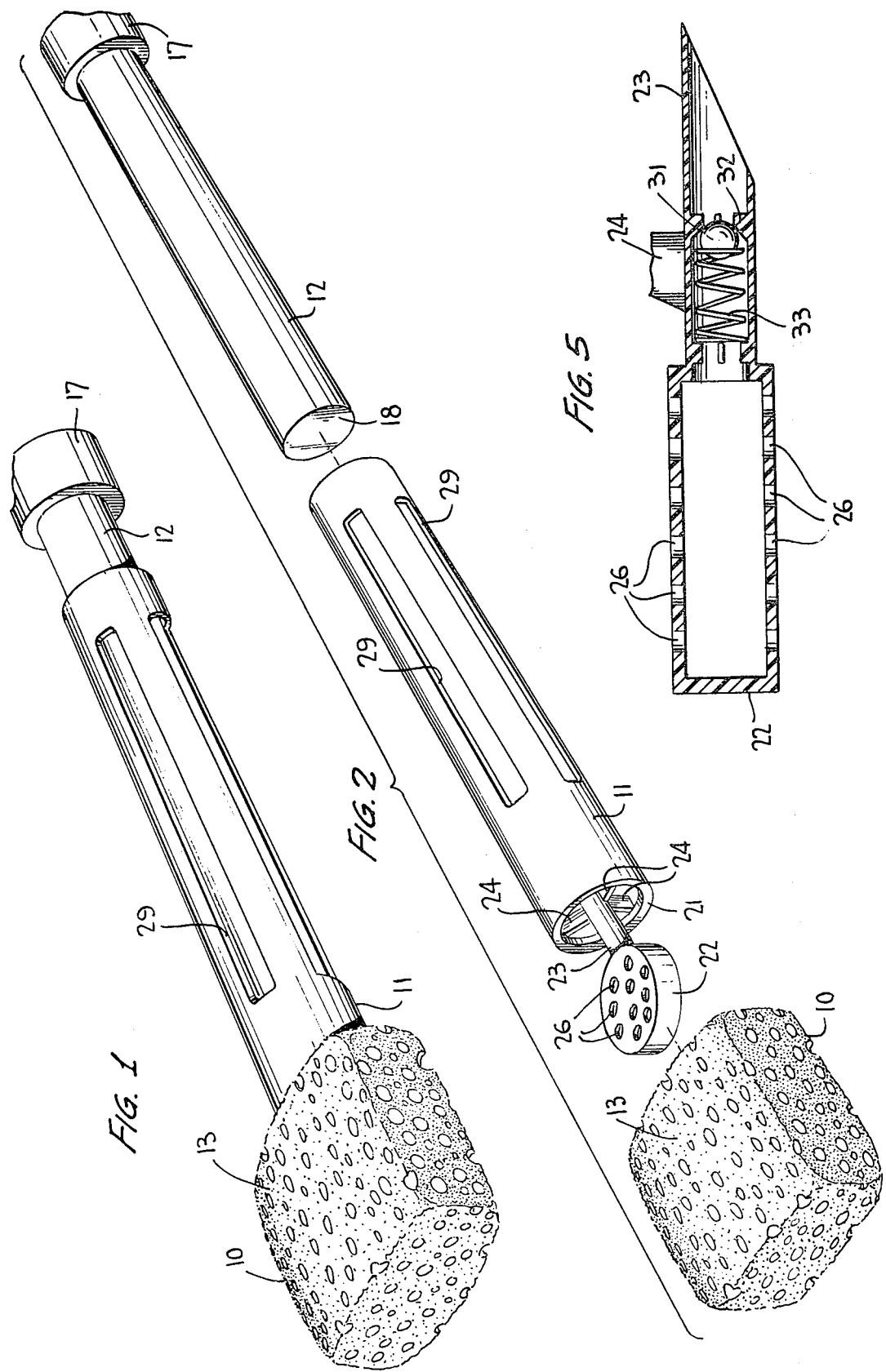

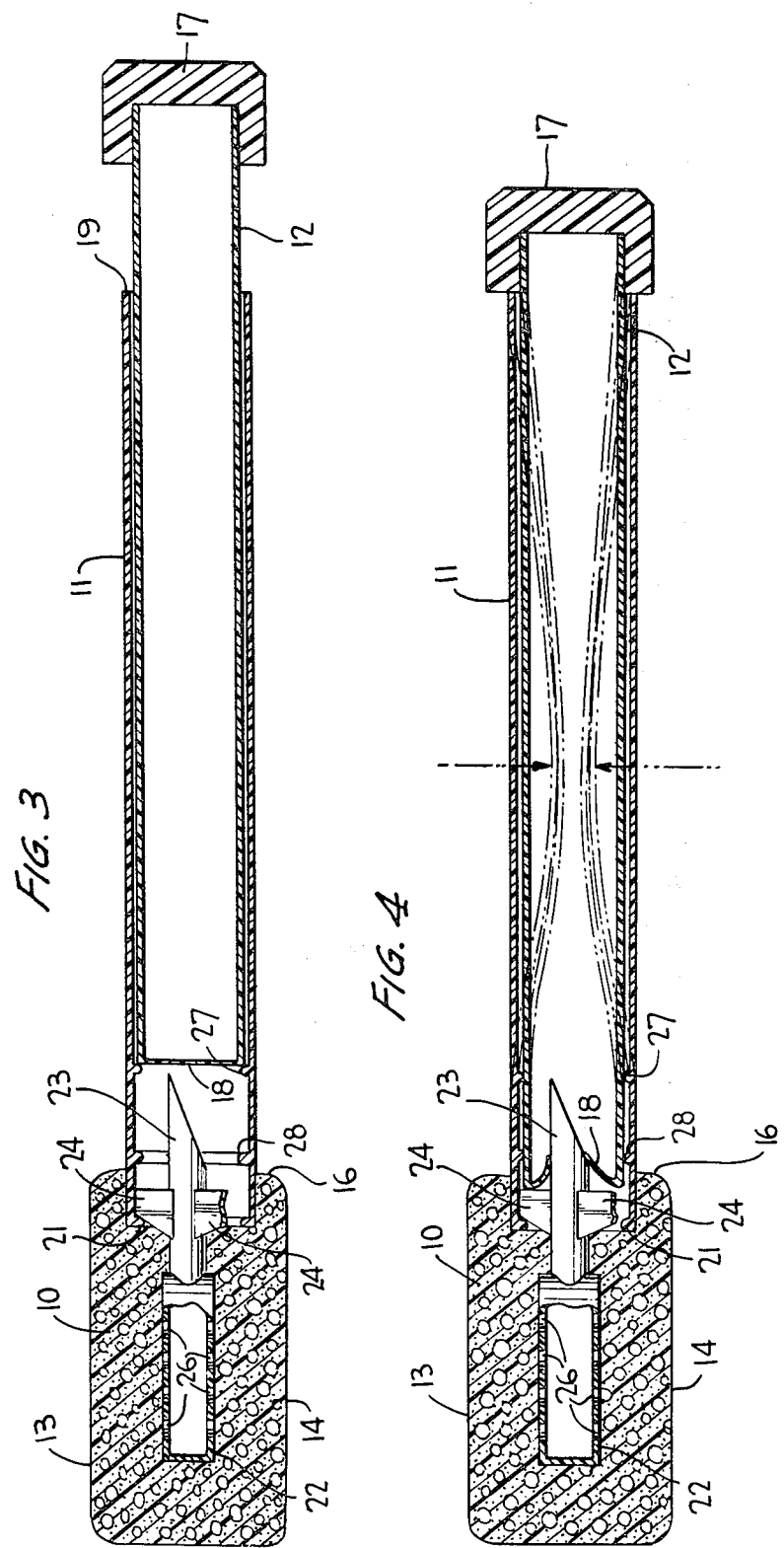

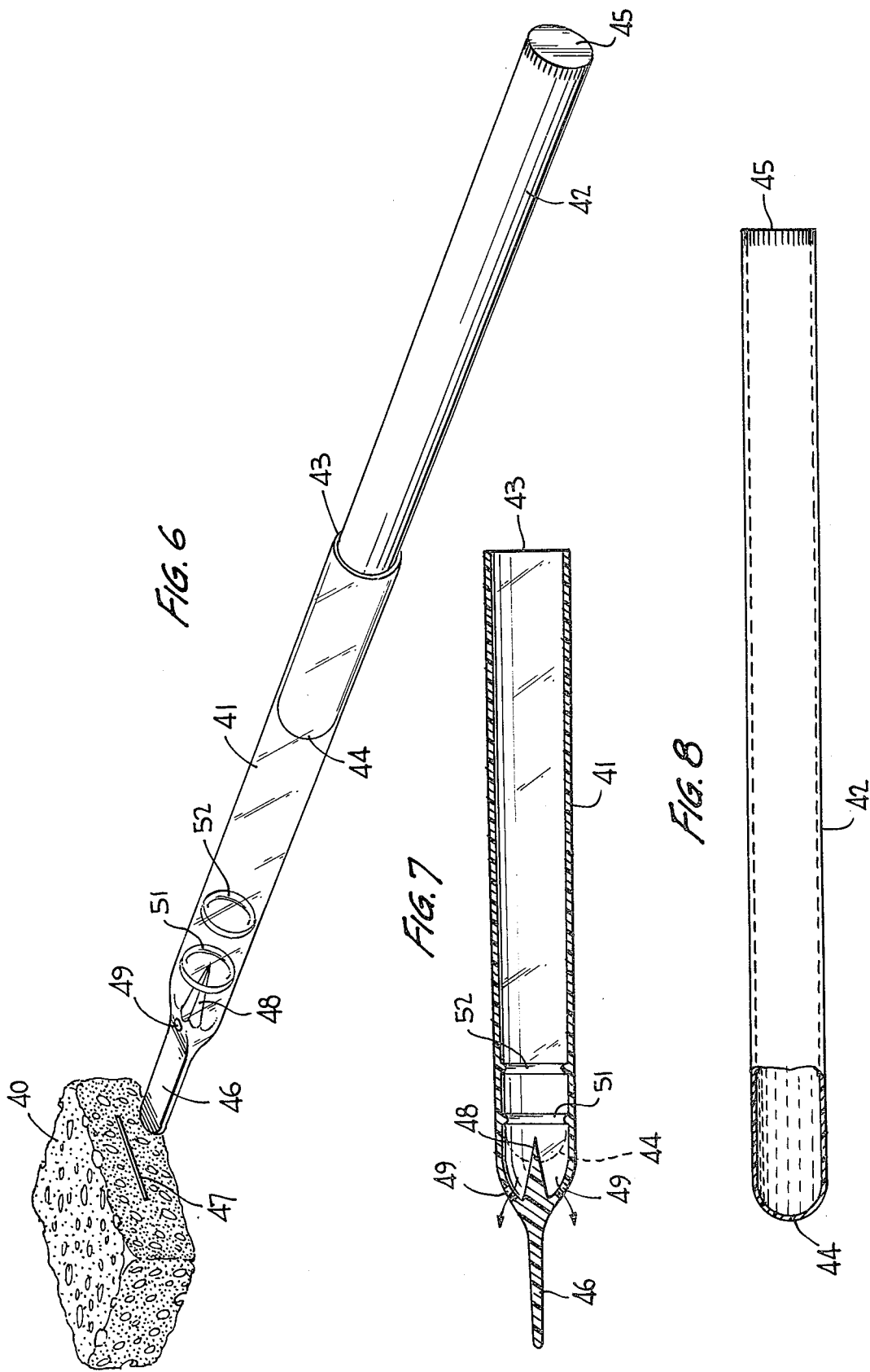

LIQUID DISPENSING DEVICE WITH CARTRIDGE-RUPTURING MEMBER

CROSS-REFERENCE TO RELATED APPLICATIONS

This application is a continuation-in-part application of U.S. patent application Ser. No. 241,486, filed Mar. 09, 1981 and entitled "Improved Liquid Dispenser," now abandoned.

TECHNICAL FIELD

The present invention relates generally to liquid dispensers and applicators of the type wherein a premeasured supply of liquid is disposed in an applicator handle and selectively dispensed through the applicator. The invention has particular applicability in the field of aseptic surgery preparation as a pre-operative surgical scrub system for use in the operating room.

BACKGROUND OF THE INVENTION

As part of the preparation for many surgical procedures, for example, a surgical operation, it is required that the affected area of the patient be antiseptically cleansed. This requirement has existed for a very long time and the procedures used to meet this requirement have changed dramatically. Originally, jars or cans of gauze sponges or cotton balls were packed, sterilized, and placed in operating rooms. These sponges and/or cotton balls were used for scrubbing procedures by holding them with sterile forceps and dipped into a pan containing a soap or antiseptic solution. After the cotton ball or sponge is saturated with the solution, it is wiped on the appropriate area. This procedure was inconvenient for a number of reasons. First, it tended to create a mess due to the open pan and the constant back and forth travel of the sponge or cotton ball between the pan and the patient. Further, the procedure took an undesirably long time and resulted in an inordinate amount of liquid being lost due to splashing, scattering, and waste. Moreover, this procedure tended to use more antiseptic solution than necessary because most medical personnel mistakenly believed that the antiseptic effect was more readily obtained if more solution was used. This is not true and, quite to the contrary, it has been noted that excess solution tends to form pools or puddles under the patient resulting in iodine burn.

Apart from the disadvantage of the forcep and sponge or cotton ball procedure, the lack of standardization of techniques resulted in considerable confusion. Eventually, certain standards did develop. Specifically, the area of incision on the patient's body must be cleaned thoroughly with a scrub or soap solution for a period between 3 to 10 minutes. Most surgical operations, other than orthopaedic surgery, require 3 minutes of scrubbing time; orthopaedic surgery requires 10 minutes of scrubbing time due to the increased risk of infection. After the scrubbing procedure, the area is dried with a sterile wipe and antiseptic solution is applied. For some procedures, other than orthopaedic surgery, the scrub portion of the procedure is eliminated and only the antiseptic solution is applied. In either case, the standard procedure for applying either the scrub or the antiseptic solution involves starting from the middle of the treated area and proceeding outward in circular or square motions, it being important never to return to a previously treated area with the same surface of the sponge. The sponge may be turned over and the same procedure started once again; that is, as long as a new sponge surface area is used, an already-prepared skin area may be re-contacted. However, one should never apply a used or contaminated sponge surface that has already been in contact with a cleanly prepared skin area.

Attempts to overcome the drawbacks described above in relation to surgical swab and/or scrub apparatus and techniques involve the development of devices in which the liquid to be applied is contained within the device itself, generally in a hollow handle. Examples of such devices may be found in the following U.S. Pat. Nos. 1,221,227; 2,333,070; 3,324,855; 3,508,547; 3,614,245; 3,774,609; 3,847,151; 3,876,314; 3,891,331; 3,896,808; 3,958,571; 4,148,318; and 4,225,254. The devices disclosed in these patents presented considerable improvements over the relatively primitive method of employing individual cotton balls or sponges with forceps and dipping these into the pan of solution as described above. However, many of the devices disclosed in the aforesaid patents are relatively complex to manufacture, thereby resulting in too high a cost for a device which is disposable after a single use. Moreover, many of the devices disclosed in these prior patents have only one available surface for the applicator sponge or swab. For example, the device disclosed in U.S. Pat. No. 4,225,254 provides a generally conical shaped sponge, thereby making it difficult to assure that the same surface area of the sponge does not contact an already treated area of the patient's skin. Moreover, the conical configuration minimizes the available surface area of the sponge. As noted, available clean, unused surface area of the preparation sponge is one of the most important factors governing the pre-surgical preparation technique.

The device disclosed in U.S. Pat. No. 3,847,151 had considerable promise toward solving most of the problems referred to above. That patent discloses a device wherein a sponge applicator is mounted on a nozzle which extends from a hollow handle containing antiseptic solution. The nozzle includes a joing which can be selectively ruptured prior to use so as to permit the solution to flow from the nozzle into the sponge. In practice, however, this device proved to have functional problems. Mass production techniques being what they are, the stress break at the rupturable joint in the nozzle was not always complete and fluid was not always available. In addition, the rupture was not always properly completed by the user of the device, again resulting in a situation where fluid was not available for use. An additional problem with this device is that the scrub solution (soap) tends to fill the sponge too slowly, whereas the swab solution (antiseptic) tends to fill the sponge too quickly. In general, the product, although well conceived, proved not to be reliable in use.

SUMMARY OF THE INVENTION

It is therefore an object of the present invention to provide a simple, inexpensive, and disposable liquid dispensing device which is capable of being used in presurgical procedures for swabbing and scrubbing. It is a further object of the present invention to provide such a device which is devoid of the disadvantages ennumerated above in the devices of the aforementioned patents. It is another object of the present invention to provide such a device useful as a swab or a scrub depending upon the selection of a replacement cartridge of the liquid to be applied. It is a particular object of the present invention to provide a surgical swab or scrub device of the type wherein liquid to be applied is contained within the handle and wherein the liquid can be reliably selectively applied to the applicator sponge.

In accordance with the present invention, an elongated tubular handle has a sponge secured to one end thereof and accepts a cartridge of liquid to be applied through its other end. A rigid spike is secured within the handle proximate its first end and is oriented to rupture the cartridge when the cartridge is fully inserted into the handle. When the cartridge is ruptured a flow path for its contained liquid is provided from within the handle to the sponge. Liquid from the cartridge can be fed to the sponge by gravity-feed or finger pressure radially applied by the user to the cartridge through the tubular handle. In one embodiment, the spike is hollow and conducts the contained liquid to an apertured chamber which projects from the tubular handle to within the sponge. The apertured chamber serves to distribute the liquid evenly during application of the liquid to the patient's body. In another embodiment, the sponge end of the handle has a flexible duck-billed or paddle-shaped terminus which is inserted into the sponge. The spike is a solid generally conical projection into the handle from the paddle. Flow from the ruptured cartridge to the sponge proceeds through plural apertures defined in the handle just rearward of the paddle and forward of the spike. In both embodiments, exertion of radially-applied pressure to the cartridge for the purpose of forcing liquid therefrom is facilitated by the provision of longitudinally extending cut-out portions of the handle. In addition, the inner wall of the handle is provided with an annular shoulder which serves as a stop for the forward end of the cartridge prior to dispensing of the liquid from the cartridge. In order to effect dispensing, the cartridge is fully inserted into the handle, forceing its forward end past the annular stop and into rupturable engagement with the spike. A check valve may be employed within the passageway between the spike and the apertured chamber to prevent back flow of contaminated solution into the sterile cartridge.

BRIEF DESCRIPTION OF THE DRAWINGS

The invention will be more fully understood, while still further objects and advantages will become apparent, in the following detailed description of embodiments thereof illustrated in the accompanying drawings, wherein:

FIG. 1 is a view in perspective of the liquid dispensing device constructed in accordance with the principles of the present inention;

FIG. 2 is an exploded view in perspective of the device of FIG. 1;

FIG. 3 is a view in longitudinal section of the device of FIG. 1 showing the device in its storage or pre-dispensing condition;

FIG. 4 is a view in section similar to that of FIG. 3 but showing the device in its dispensing mode;

FIG. 5 is a detailed view in section of a portion of the device of FIGS. 1-4, illustrating a check valve employed therein;

FIG. 6 is a view in perspective of another embodiment of the present invention;

FIG. 7 is a view in section of the handle member of the embodiment of FIG. 6; and FIG. 8 is a side view in partial section of the cartridge member of the embodiment of FIG. 6.

DESCRIPTION OF THE PREFERRED EMBODIMENTS

Referring to FIGS. 1-5 of the drawings in greater detail, a dispenser embodiment of the present invention comprises three (3) major parts, namely: a sponge applicator 10; a tubular handle 11; and a cartridge 12. The sponge 10 may be made from a variety of medically accepted sponge-like materials having a wide density range and coarse or fine textures. Coarse texture may be emloyed for scrubbing because it is more abrasive; the finer texture may be utilized for application of antiseptic solution. For general use, sponge 10 is ideally 2 inches square by 1 inch thick; however, these dimensions are provided by way of example only and size is by no means a limiting factor on the present invention. The sponge is preferably configured to have 2 large measure flat application surfaces 13 and 14, but again the configuration is not to be considered limiting on the scope of the present invention. Surfaces 13 and 14 may be generally rectangular, as shown, or may be circular, oval, triangular, etc. Sponge 10 is adapted to receive one end of tubular handle 11 through a suitably provided opening in an end surface 16 of the sponge which resides generally perpendicular to the application surfaces 13 and 14. The end surface 16 of sponge 10 may be suitably die-cut in order to receive the end of handle member 11 in the manner described below. For example, sponge 10 may be cut into a $2''\times4''\times\frac{1}{2}''$ piece which is folded in half and glued on portions of the inner surface to cover the received portion of handle 11. Alternatively, sponge 10 may be die-cut into a piece $2''\times2''$ and slotted at surface 13 to permit insertion of the handle member 11. Adhesive may be emloyed to stabilize the sponge onto the handle member.

Cartridge member 12 is a generally tubular member whose outside periphery matches the inside periphery of a portion of tubular handle 11. The outside dimensions of cartridge 12 substantially match the inside dimensions of tubular handle 11 so that the cartridge can freely slide longitudinally within the handle member. The overall size can range from as little as a 5 ml capacity to as large as a 240 ml capacity. In this regard, the entire unit can be selected to be of the appropriate size for the desired amount of liquid to be administered. For a sponge 10 having dimensions of $2''\times2''\times1''$, the average capacity of the cartridge would be 30 ml. Cartridge 12 may be produced on a form, fill and seal machine in a continuous operation. Under such circumstances, the container is blow molded, filled with the desired fluid, and sealed in continuous steps of one overall operation. The configuration of the cartridge should not be considered limited and may be fabricated by any plastic-forming equipment, as long as the resulting product has the overall density required to contain the liquid employed. The tubular cartridge should have a plastic density which permits simple placement into the tubular handle while providing sufficient rigidity to permit sliding movement through the handle. The cap 17 for cartridge 12 is disposed at one end thereof and may be formed integrally with the cartridge, if desired. The opposite end 18 of the cartridge may be of the same density as the overall cartridge but in any event, must be suitable to permit rupture and penetration of the cartridge in the manner described herein below.

In this respect, the forward end 18 of the cartridge is preferably thinner than the cap 17 which should be considerably heavier to afford a more rigid plastic form and thereby facilitate application of a pushing force required to displace cartridge 12 with the handle 11 so that forward end 18 can be ruptured.

Handle member 11 comprises, for the most part, a rigid plastic tube having an open end 19 adapted to receive cartridge 12 therein when the cartridge is inserted with its forward end 18 first. The opposite end 21 of handle 11 extends partway into sponge 10 and includes, preferably formed as an integral part thereof, a dispensing chamber 22. The dispensing chamber projects forwardly of handle 11 into sponge 10. A tubular spike 23 extends rearwardly from the dispensing chamber 22 into the tubular portion of handle 11 and is provided with a plurality of radially-extending stabilizing fins 24 which fixedly engage the interior surface of the tubular handle member 11. As noted above, it is preferable that the dispensing chamber 22, spike 23, and stabilizing fins 24 be formed integrally with tubular section 11 by means of an appropriate plastic-forming technique; alternatively, these components may form a part of a separate unit which is secured at the remote ends of stabilizing fins 24 to the interior wall of tubular member 11 by means of a suitable adhesive material or the like. For the latter configuration, an annular lip is formed, as shown, at the forward end 21 of tubular handle member 11 to retain the fins 24 in proper position.

Dispensing chamber 22 may take the form of a shallow cylinder, as shown, or any other suitable configuration. In the preferred shallow cylindrical configuration shown, the opposite circular ends of the chamber are provided with a plurality of apertures 26 which provide fluid communication between the interior of chamber 22 and the surrounding interior of sponge 10. The primary function of dispensing chamber 22 is to provide free flow of pressurized fluid therein into the sponge to soak the sponge for application to the appropriate body surface area. A secondary function of dispensing chamber 22 is to provide sufficient rigidity to the sponge during application of the liquid from the sponge to the patient's body. This latter function is best served when the apertured ends of dispensing chamber 22 have the largest possible surface area. However, smaller dispensing chambers can be utilized with effective results.

Spike 23 is in the form of a tube which projects rearwardly from dispensing chamber 22 and has its interior in flow communication therewith. The end of spike 23 remote from chamber 22 is tapered to a fine point, much like a conventional intravenous spike.

A narrow annular shoulder 27 projects radially inward from the interior wall of tubular handle 11 at an axial location just beyond the tip of spike 23. More specifically, the tip of spike 23 is spaced a slightly shorter distance from end 21 of tubular handle 11 than is the annular lip 27. Lip 27 serves as a flexible stop for end 18 of cartridge 12. Specifically, as illustrated in FIG. 3, the outer edges of the forward end 18 of cartridge 12 abut lip 27 in the stand-by condition of the unit. Lip 27 thereby spaces the forward end 18 of the cartridge from the point of spike 23. When it is desired to apply fluid from the cartridge to a surface area of a patient, or the like, cartridge 12 is pushed forward within tube 11, causing lip 27 to flex and permitting the forward end 18 of cartridge 12 to move forwardly and be ruptured by the point of spike 23. This is best illustrated in FIG. 4. The hollow spike 23 enters the cartridge via cartridge end 18 and permits liquid from the cartridge to flow through the spike to the dispensing chamber 22 where it flows through apertures 26 to soak the sponge 10. A dealing ring, for example, an O-ring 28, projects from the interior surface of handle member 11 radially inward at an axial location between end 21 and stop lip 27. The sealing ring 28 prevents fluid from the sponge from flowing back past sealing member 28 into handle 11.

Tubular handle 11 is provided with a plurality of longitudinally-extending cut-out slots 29. These slots are provided to permit radial compression of the handle 11 so that cartridge 12 may be compressed and liquid forced therefrom into the sponge. It will be appreciated that this compression can be readily achieved by grasping handle 11 in the palm of one's hand and squeezing the hand closed. Alternatively, liquid feed from cartridge 12 to sponge 10 may be effected by gravity flow by simply holding the unit with end 17 upward.

In some applications, it may be desirable to prevent back-flow of dispensed liquid from the sponge and/or dispensing chamber 22 to the cartridge 12. In such cases, a check valve may be supplied within the hollow spike 23 as illustrated in FIG. 5. Sepcifically, a ball member 31 is disposed within the hollow spike 23 and is biased rearwardly toward the sharp spike end by means of a spring 33. The rearwardly biased ball member 31 sits in a valve seat 32 in the non-operating position of the unit to block flow through the hollow spike. If fluid in the cartridge 13 is pressurized, such as by comprssing the handle 11, ball member 31 is unseated from seat 32 by the pressurized liquid which is then permitted to flow into the dispensing chamber 22. When the pressure of the liquid in chamber 22 is greater than the pressure of the liquid in cartridge 12, as would be necessary to result in a reversed flow of the liquid, spring 33 forces ball member 31 to its closed position to preclude reverse flow.

Referring now to FIGS. 6-8 of the accompanying drawings, a second embodiment of the dispenser of the present invention is illustrated. In this embodiment, the primary difference from the embodiment described above relates to the forward or sponge-end of the handle member and the manner in which the sponge is supported and dispensed liquid flows to the sponge. Specifically, a second embodiment includes a sponge applicator 40, a hollow tubular handle 41 and a cartridge 42 which is slidably received by handle 41 through open rearward 43 of the handle. Sponge 40 is similar in function and configuration to sponge 10 of the embodiment illustrated in FIGS. 1-5 and partakes of all of the design features and considerations set forth above for sponge 10. Likewise, cartridge 42 is functionally and structurally similar to cartridge 12 illustrated and described in relation to the embodiment of FIGS. 1-5. In the embodiment of FIGS. 6-8, the forward end 44 of 42 is rounded and readily susecptible to puncture by a spike in the manner described below. The rearward end 45 of cartridge 42 is more rigid to facilitate insertion of cartridge 42 into handle 41 by pushing the rearward end 45 appropriately.

Handle member 41 is similar in function to handle 11 in the embodiments of FIGS. 1-5. As noted above, the rearward end 43 of handle 41 is open to receive the forward end of cartridge 42. The forward end of handle 41 tapers to form a paddle or paddle-shaped projection member 46 which projects forwardly of handle member 41. This paddle-shaped projection 46 is adapted to be received in a suitably provided slot 47 in sponge 40. Projection 46 thus serves to support sponge 40 into which it projects. For this purpose, projection 46 is made somewhat flexible to permit relative flexure between the sponge 40 and handle member 41. A conical spike 48 projects rearwardly of projection 46 into the interior of the forward end of handle 41. Spike 48 serves the purpose of rupturing the forward end 44 of cartridge 42 when that cartridge is sufficiently inserted into handle member 41. To this end, although spike 48 is shown as a sharp, conical projection, it may take other forms, such as a "bullet-nosed" configuration. The important point is that the rearward most part of spike 48 should be sufficiently sharp to permit it to rupture forward end 44 of the cartridge. Spike 48 differs from spike 23 in the embodiment of FIGS. 1–5 in that it does not provide an internal flow path whereby fluid from cartridge 42 can flow out of handle 41; in other words, spike 48 is not hollow. Instead, the forward end of handle 41, rearwardly of projection 46, is provided with a plurality of apertures 49 through which liquid can escape from the interior of handle 41 after it has been squeezed from the ruptured cartridge 42. Apertures 49 are disposed at a longitudinal position of handle 41 which is inserted within slots 47 of sponge 40 so that all of the liquid which escapes from apertures 49 is absorbed into sponge 40.

A narrow annular shoulder 51 projects radially inward from the interior wall of tubular handle 41 at an axial location just rearward of the rearward extremity of spike 48. The similar annular shoulder 52 projects radially inward from the interior wall of handle 41 at a location spaced slightly rearward of shoulder 51. Shoulder 52 serves as a stop for forward end 44 of cartridge 42 when the cartridge is inserted in handle 41. To this end, the axial position of shoulder 52 is such that when it stops further insertion of the cartridge into handle 41, the forward end 44 of the cartridge is spaced from the rearward extremity of spike 48. In the manner similar to that described above in relation to the embodiment of FIGS. 1–5, cartridge 42 can be forced beyond the stop shoulder 52 so that the forward end 44 of the cartridge 42 can be punctured by spike 48. Shoulder 51 serves as a fluid seal, in conjunction with the peripheral wall of the ruptured cartridge 42, to prevent the fluid from the ruptured cartridge from flowing rearwardly in the handle member 41. Handle member 41 may be provided with longitudinally-extending cut-out slots, such as slots 29 in handle member 11, to facilitate radial compression of handle member 41 and thereby force liquid from cartridge 42 through apertures 49 into sponge 40.

In a typical, but by no means limiting configuration of the embodiment of FIGS. 6–8, the various parts have the dimensions noted below. Cartridge 42 is 8 inches long and has a ⅝ inch diameter. Sponge 40 has top and bottom surfaces which are 1¾" square and is ½" deep. The overall length of handle member 41 is 6 5/16", the paddle-shaped projection 46 being 1" long. The inner diameter of handle 41 is ⅝" and the thickness of the walls of handle 41 is approximately 0.050". The length of spike 48 is approximately ⅜". The tubular handle 41 may, if desired, have a taper on the order of 0.5° from rearward end 43 toward paddle member 46 in order to facilitate insertion of cartridge 42 and eventual retention of the cartride in the handle. The paddle member or projection 46 is preferably as thin as possible to enhance flexibility and the end of the projection is preferably rounded rather than squared-off. The size of apertures 49 depends upon the desired flow characteristics for the device in view of the liquid being dispensed.

The unit as described, is simple and inexpensive to fabricate and is therefore readily disposable after a single use. Specifically, the unit in the optimal case may be fabricated from only three (3) separate components, namely: sponges 10 and 40; cartridges 12 and 42, which may be fabricated integrally with actuating ends 17 and 45; and tubular handles 11 and 41, which may be fabricated integrally with dispensing chamber 22, spike 23, positioning fins 24 and projection 46 and spike 48. Cartridges, of course, may be interchangeable so that a variety of different liquids may be employed during the same procedure, if an insufficient amount of liquid has been applied. The cartridges are easy to change and remain sealed and sterile until used. The user of the device need not wear a surgical glove in view of the sterility of the cartridge arrangement. The unit may be simply activated by merely grasping the handle in one's hand and gently rapping the end of the cartridge on a hard surface so as to force the forward end 18 of the cartridge against spike 23. Actuation is thus reliable and easily effected and the liquid to be dispensed flows freely to the sponge.

While, we have described and illustrated specific embodiments of our invention, it will be clear that variations of the details of construction which are specifically illustrated and described may be resorted to without departing from the true spirit and scope of the invention as defined in the appended claims.

We claim:
1. A liquid dispensing device comprising:
   an elongated member having a hollow tubular handle portion and first and second ends, said first end being open to said tubular handle portion, said second end being configured as a paddle-like member formed integrally to said tubular handle portion and being transversely flexible relative to said tubular handle portion;
   an absorbent sponge-like member disposed about said paddle-like member;
   an elongated fluid-containing cartridge adapted for longitudinal slidability in said tubular handle portion of said elongated member, said cartridge having a rupturable forward end by which it is inserted into said open end of said elongated member;
   flow passage means for providing flow communication from within said tubular handle portion to said sponge-like member along opposite sides of said paddle-like member; and
   a cartridge-rupturing member positioned in said tubular handle portion proximate said second end and including a projection portion within said tubular handle portion to rupture said forward end of said cartridge in response to a predetermined slidable insertion of said cartridge into said tubular handle portion;
wherein said tubular handle portion includes a generally cylindrical interior surface along which said elongated cartridge is longitudinally slidable, said tubular handle portion further comprising an annular stop member projecting radially inward from said internal surface for resiliently engaging said forward end of said cartridge at a location wherein the cartridge is spaced from said projecting portion of said cartridge-rupturing member, the resilient engagement of said forward end by said annular stop member being overcome by force exerted longitudinally on said cartridge in the direction of said projecting portion to permit passage of said forward end of said cartridge into rupturable engagement with said projecting portion.

2. The liquid dispensing device according to claim 1, wherein said flow passage means comprises plural apertures defined in said hollow handle portion proximate said paddle-like member.

3. The liquid dispensing device according to claim 1, wherein said cartridge-rupturing member comprises a spike extending axially within said tubular handle portion from said paddle-like member.

* * * * *